United States Patent
Romero Amandi De Sousa et al.

(10) Patent No.: US 10,927,193 B2
(45) Date of Patent: Feb. 23, 2021

(54) GELLAN GUM-BASED HYDROGELS, METHODS AND USES THEREOF

(71) Applicant: STEMMATTERS, BIOTECNOLOGIA E MEDICINA REGENERATIVA, S.A., Barco GMR (PT)

(72) Inventors: Rui Pedro Romero Amandi De Sousa, Matosinhos (PT); Cristina Correia, Sao Mamede Escariz (PT); David Alexander Learmonth, Alfena (PT); Rui Luis Gonçalves Dos Reis, Oporto (PT)

(73) Assignee: STEMMATTERS, BIOTECNOLOGIA E MEDICINA REGENERATIVA, Barco GMR (PT)

( * ) Notice: Subject to any disclaimer, the term of this patent is extended or adjusted under 35 U.S.C. 154(b) by 12 days.

(21) Appl. No.: 16/065,180

(22) PCT Filed: Dec. 22, 2016

(86) PCT No.: PCT/IB2016/057952
§ 371 (c)(1),
(2) Date: Jun. 22, 2018

(87) PCT Pub. No.: WO2017/109755
PCT Pub. Date: Jun. 29, 2017

(65) Prior Publication Data
US 2019/0010254 A1    Jan. 10, 2019

(30) Foreign Application Priority Data
Dec. 22, 2015   (PT) .......................... 109054

(51) Int. Cl.
| | | |
|---|---|---|
| *C08B 37/00* | (2006.01) | |
| *A61L 27/20* | (2006.01) | |
| *A61K 35/28* | (2015.01) | |
| *A61L 27/38* | (2006.01) | |
| *A61L 27/52* | (2006.01) | |
| *A61K 9/00* | (2006.01) | |
| *A61K 31/715* | (2006.01) | |
| *A61L 27/54* | (2006.01) | |

(52) U.S. Cl.
CPC .......... *C08B 37/006* (2013.01); *A61K 9/0019* (2013.01); *A61K 31/715* (2013.01); *A61K 35/28* (2013.01); *A61L 27/20* (2013.01); *A61L 27/3834* (2013.01); *A61L 27/52* (2013.01); *A61L 27/54* (2013.01); *A61L 2400/06* (2013.01); *A61L 2430/02* (2013.01)

(58) Field of Classification Search
CPC .. A61L 27/20; A61L 2400/06; A61L 2430/02; A61L 27/3834; A61L 27/52; A61L 27/54; A61K 35/28; A61K 37/715; A61K 9/0019; C08L 5/00; C08B 37/006
See application file for complete search history.

(56) References Cited

U.S. PATENT DOCUMENTS

| | | | | |
|---|---|---|---|---|
| 6,172,219 | B1* | 1/2001 | Callegaro | ............. A23L 3/3463 536/123.1 |
| 2011/0293584 | A1* | 12/2011 | De Bruijn | ........... A61L 27/3821 424/93.7 |
| 2016/0095958 | A1* | 4/2016 | Grayson | ................. A61L 27/52 424/426 |

FOREIGN PATENT DOCUMENTS

| | | |
|---|---|---|
| WO | 2005084610 A2 | 9/2005 |
| WO | 2011119059 A1 | 9/2011 |
| WO | 2015173783 A1 | 11/2015 |

OTHER PUBLICATIONS

Product information for Gelzan TM from Sigma https://www.sigmaaldrich.com/catalog/product/sigma/g1910?lang=en&region=US downloaded Nov. 22, 2019 (Year: 2019).*
Defintion of a hydrogel down loaded from https://www.merriam-webster.com/dictionary/hydrogel on Nov. 24, 2019 (Year: 2019).*
Kim et al. J. Biomed. Materials Research (2009) 88A: 967-975 (Year: 2009).*
Coutinho et al. "Modified Gellan Gum hydrogels with tunable physical and mechanical properties." Biomaterials 31.29 (2010): 7494-7502.
D'Este et al. "A systematic analysis of DMTMM vs EDC/NHS for ligation of amines to hyaluronan in water." Carbohydrate Polymers 108 (2014): 239-246.
Doner. "Rapid purification of commercial gellan gum to highly soluble and gettable monovalent cation salts." Carbohydrate Polymers 32.3-4 (1997): 245-247.
Ferris et al. "Modified gellan gum hydrogels for tissue engineering applications." Soft Matter 9.14 (2013): 3705-3711.
Hamcerencu et al. "Synthesis and characterization of new unsaturated esters of Gellan Gum." Carbohydrate Polymers 71.1 (2008): 92-100.
Oliveira et al. "Gellan gum injectable hydrogels for cartilage tissue engineering applications: in vitro studies and preliminary in vivo evaluation." Tissue Engineering Part A 16.1 (2009): 343-353.

(Continued)

*Primary Examiner* — Susan M Hanley
(74) *Attorney, Agent, or Firm* — Leason Ellis LLP

(57) ABSTRACT

The present disclosure relates to gellan gum and gellan gum-based hydrogels (GG-based hydrogels) for promoting chondrogenic, osteogenic and adipogenic differentiation of human mesenchymal stem cells, preferentially osteogenic. The present disclosure also relates to a composition for use in bone, cartilage and soft tissue engineering and regenerative medicine, preferably for use in bone.

15 Claims, 2 Drawing Sheets

(56) References Cited

OTHER PUBLICATIONS

Rada et al. "Chondrogenic potential of two hASCs subpopulations loaded onto gellan gum hydrogel evaluated in a nude mice model." Current Stem Cell Research & Therapy 8.5 (2013): 357-364.
Recuenco et al. "Gellan sulfate inhibits Plasmodium falciparum growth and invasion of red blood cells in vitro." Scientific Reports 4 (2014): 4723.
Silva-Correia et al. "Gellan gum-based hydrogels for intervertebral disc tissue-engineering applications." Journal of Tissue Engineering and Regenerative Medicine 5.6 (2011): e97-e107.
Tsaryk et al. "Biological performance of cell-encapsulated methacrylated gellan gum-based hydrogels for nucleus pulposus regeneration." Journal of Tissue Engineering and Regenerative Medicine 11.3 (2014): 637-648.

\* cited by examiner

| | Chondrogenic |
|---|---|
| Gellan Gum 1% w/V |  |
| Methacrylated Gellan Gum 2% w/V |  |
| | Osteogenic |
| Gellan Gum 1% w/V |  |
| Methacrylated Gellan Gum 2% w/V |  |
| | Adipogenic |
| Gellan Gum 1% w/V |  |
| Methacrylated Gellan Gum 2% w/V |  |

| | Chondrogenic |
|---|---|
| Gellan Gum 1% w/V |  |
| Methacrylated Gellan Gum 2% w/V |  |
| | Osteogenic |
| Gellan Gum 1% w/V |  |
| Methacrylated Gellan Gum 2% w/V |  |
| | Adipogenic |
| Gellan Gum 1% w/V |  |
| Methacrylated Gellan Gum 2% w/V |  |

GELLAN GUM-BASED HYDROGELS, METHODS AND USES THEREOF

CROSS-REFERENCE TO RELATED APPLICATIONS

This application is a U.S. National Stage Application under 35 U.S.C. § 371 of International Patent Application No. PCT/1132016/057952, which was filed on Dec. 22, 2016, which claims priority to Portuguese Patent Application No. 109054, which was filed on Dec. 22, 2015, both of which are hereby incorporated by reference in their respective entireties.

TECHNICAL FIELD

The present disclosure relates to self-inducing gellan gum-based hydrogels (GG-based hydrogels) for promoting chondrogenic, osteogenic and adipogenic differentiation of human mesenchymal stem cells, preferentially osteogenic. The present disclosure also relates to an injectable composition for use in bone, cartilage and soft tissue engineering and regenerative medicine, preferably for use in bone regeneration.

BACKGROUND

Previous studies with gellan gum-based hydrogels have shown that these serve as effective matrices for encapsulation of human articular chondrocyctes, supporting growth and deposition of cartilage extracellular matrix (Oliveira, 2009).

Chondrogenic differentiation of human adipose stromal/stem cell (hASC) subpopulations within gellan gum-based hydrogels and production of chondrogenic extracellular matrix has been reported (Rada, 2013).

Whereas chondrogenesis has traditionally been the principal lineage of research focus to date, little understanding exists with respect to hASC behaviour when induced into the other two lineages—osteogenic and adipogenic—within the gellan-based hydrogels alone, either with respect to cell viability or to extracellular matrix deposition.

These facts are disclosed in order to illustrate the technical problem addressed by the present disclosure.

General Description

The disclosure relates to self-inducing gellan-based hydrogels which are extremely effective at improving cell viability and promoting chondrogenic, osteogenic and adipogenic differentiation of mesenchymal stem cells, particularly osteogenic differentiation. In particular, the disclosure relates to a gellan gum hydrogel prepared by ionic or photo-crosslinking of a gellan gum having a composition according to Formula I;

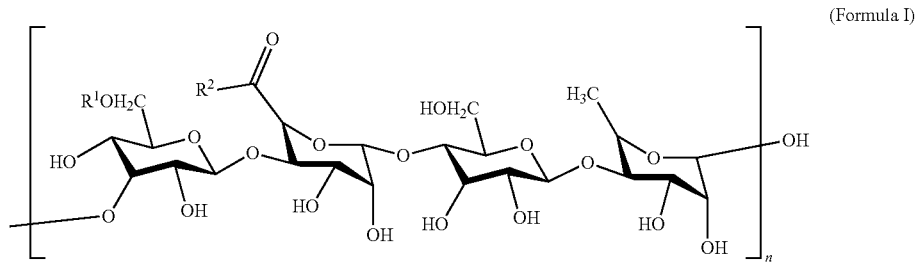

(Formula I)

wherein
$R^1$ signifies hydrogen, sulphate or $CO-C(=CH_2)CH_3$ and,
$R^2$ signifies hydroxyl, $ONa^+$, $OK^+$ or $OLi^+$ or is a group chosen from $-O-CH(-CH_2OH)-CH_2-O-C(=O)-C(=CH_2)-CH_3$ or $NHNHCO(CH_2)_{n'}CONHNH_2$ where n' signifies an integer chosen from one to ten,
preferably, wherein n is an integer from 700 to 4000.

Gellan gum (GG) is a microbial anionic heteropolysaccharide consisting of a glucose-glucuronic acid-glucose-rhamnose tetrasaccharide repeating unit and can be found in two forms, acetylated and deacetylated. Preferably the gellan gum is deacylated.

In a preferred embodiment, the molecular weight of gellan gum may range from 500 KDa to 2500 KDa.

An aspect of the present subject-matter is a gellan comprising the structure according to Formula I for use in chondrogenic and/or osteogenic and/or adipogenic differentiation of human mesenchymal stem cells, in particular in the treatment of a diseases that is positively influenced by the chondrogenic and/or osteogenic and/or adipogenic differentiation of human mesenchymal stem cell, more in particular for use in bone repair, even more in particular for use in the treatment of bone fracture, bone repair or in the treatment of osteopathies or in the treatment of osteochondritis.

It has now been surprisingly found that certain hydrogels formed by ionic or photo-crosslinking of gellan gum precursor materials are extremely effective at improving cell viability and promoting chondrogenic, osteogenic and/or adipogenic differentiation of mesenchymal stem cells, preferably in promoting osteogenic differentiation of mesenchymal stem cells in the absence of further biological stimuli or cues.

In a preferred embodiment for better results, the gellan gum/hydrogel disclosed are for use in bone regeneration by promoting angiogenesis and bone turnover, preferably in fracture repair.

In a preferred embodiment, the hydrogel precursor materials are prepared from purified gellan gum. Commercial gellan gum contains divalent cation impurities which can be removed by treatment with an appropriate ion exchange resin, converting the gellan gum to the free carboxylic acid form. Treatment of the free carboxylic acid with aqueous sodium hydroxide solution leads to the formation of the monovalent sodium salt form of gellan gum which is readily soluble in water at room temperature, making it suitable for cell encapsulation at physiological temperature and for further chemical modification.

In another preferred modification, the thus obtained purified gellan gum can be modified through further chemical synthesis. For example, methacrylation at either the glucose (Coutinho, 2010) or glucuronic acid residues (Silva-Correia, 2011) is possible.

In another preferred embodiment, thus obtained purified gellan gum can be modified through sulphation by methods known to those skilled in the art (Recuenco, 2014).

In another preferred embodiment, thus obtained purified gellan gum can be modified through amidation with amines and hydrazides by methods known to those skilled in the art. For example, a coupling agent such as 4-(4,6-dimethoxy-1,3,5-triazin-2-yl)-4-methylmorpholinium chloride (DTMMCl) may be used to couple the carboxylic acid group of gellan gum with amine-containing substituents (D'Este, 2014).

By varying the reaction conditions, reaction stoichiometry and reaction times, it is possible to obtain different degrees of substitution of the gellan gum. In a particularly preferred embodiment, the degree of substitution by either $R^1$ or $R^2$ is between 0.5-20%, wherein said degree of substitution is calculated as described previously (Hamcerencu, 2008).

In an embodiment, the degree of substitution by either $R^1$ or $R^2$ is between 0.5-20% and said degree of substitution is achieved under the following conditions: the reaction stoichiometry is between 1 and 50 molar equivalents of reactant relative to gellan gum starting material the reaction temperature is between 0° C. to 100° C. and the reaction time is between 1 and 96 hours. Suitable solvents for the reactions include water, polar aprotic solvents such as dimethyl sulfoxide and N-methylpyrrolidinone, or mixtures thereof.

Crosslinking of the gellan gum derivatives described above can be mediated ionically by physiologically relevant monovalent or divalent cations such as $Na^+$, $K^+$, $Ca^{2+}$ or $Mg^{2+}$, or mixtures thereof. Alternatively, where unsaturated hydrocarbon groups are present, as in methacrylated gellan gum, covalent crosslinking can be achieved by photo-crosslinking in the presence of ultraviolet light and a suitable photoinitiator such as Irgacure 2959, among others.

Differentiation of mesenchymal stem cells within tissue-specific lineages is commonly evaluated by the deposition of tissue-specific extracellular matrix (ECM) components. Herein, expression of these ECM markers was evaluated upon in vitro tri-lineage induction of hASC when encapsulated in the above mentioned gellan gum-based hydrogels.

In a preferred embodiment for cell encapsulation, the concentration of the gellan gum hydrogel is between 0.5%-5% w/V. Preferably, the concentration of the gellan gum hydrogel is between 0.5%-2.5% w/V, more preferably 1.25%-2% w/V.

Another aspect of the present subject matter, is related to a hydrogel comprising a gellan gun containing Formula I structure.

In a preferred embodiment the gellan gum hydrogel may be constituted in water, preferably sterile distilled water, most preferably sterile water for injection.

In a preferred embodiment for cell encapsulation, the concentration of cells, in particular human adipose stromal/stem cells, is between one million and fifty million cells, More preferably, the concentration of human adipose stromal/stem cells, is between one million and ten million cells. Even more preferably, the ratio of the gellan gum hydrogel and cells is in the range 9:1 (V/V), most preferably 8:2 (V/V).

In a further preferred embodiment, hydrogel crosslinking can be achieved by ionic crosslinking, in particular by addition of physiologically acceptable media such as sodium chloride solution, phosphate buffer saline, Ringer solution or cell culture medium suitable for human mesenchymal stem cells to the gellan gum solution in sterile water, preferably in the ratio 8:2. Most preferably, hydrogel crosslinking is achieved by addition of cell culture medium containing human adipose stromal/stem cells in two parts to a solution of the gellan gum (8 parts), to form an initially injectable solution which gels in situ within the body.

Another aspect of the present subject matter, is related to a composition for use in the treatment of a diseases that is positively influenced by the chondrogenic and/or osteogenic and/or adipogenic, comprising a matrix containing the gellan gum of the present subject-matter or the hydrogel of the present subject-matter and human adipose mesenchymal stromal/stem cells. Preferably, wherein said human adipose mesenchymal stromal/stem cells are encapsulated within the gellan gum.

Another aspect of the present subject matter is related to a mesh, disc, scaffold or membrane comprising the composition of the present subject-matter.

Another aspect of the present subject matter is related to a kit for bone regenerative medicine comprising a matrix containing the gellan gum of the present subject-matter or the hydrogel of the present subject-matter, mammalian cells in particular human mesenchymal stem cells.

BRIEF DESCRIPTION OF THE FIGURES

The disclosure will now be described in detail, by way of example only, with reference to the following Figures.

DETAILED DESCRIPTION

Figure 1:
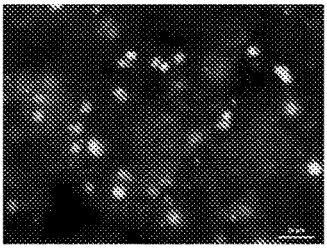
FIG. 1. Microscopic imaging of Live/Dead staining of hASC encapsulated in GG-based hydrogels, and induced into chondrogenic, osteogenic and adipogenic lineages for 21 days in vitro. Live: Green large cells; Dead: Red small dots (DNA). Magnification: 200×
Figure 1:
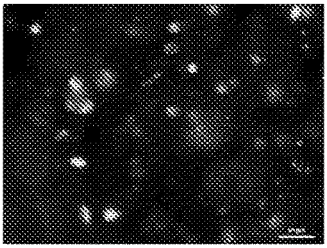
Figure 1:
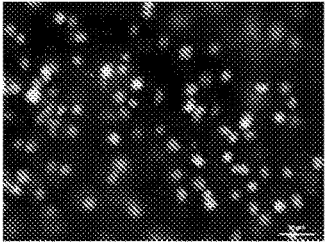
Figure 1:
Figure 1:
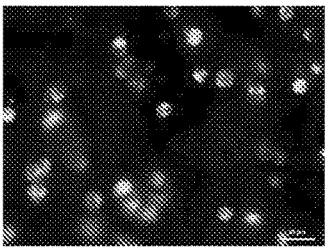
Figure 1:
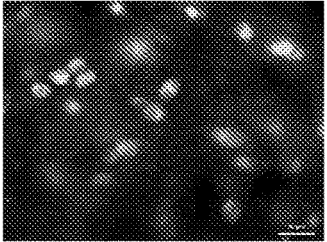

FIG. 1 represents live/dead imaging of hydrogel cross-sections after tri-lineage induction for 21 days in vitro. Green large live cells are detected by calcein AM, while propidium iodide stains red the DNA of dead cells with compromised cell membranes. Cell viability is evident within the three differentiation lineages, independently of the GG-based hydrogel.

Figure 2:
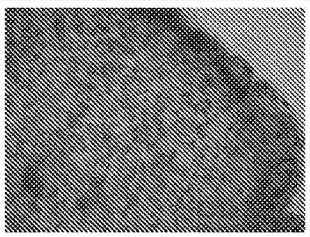
FIG. 2. Microscopic imaging of lineage specific staining of differentiated hASC within GG-based hydrogels after 21 days in vitro culture: Chondrogenesis—Safranin O staining of glycosaminoglycans (red); Osteogenesis—Alizarin Red staining of calcium (red); Adipogenesis—Oil Red O staining of lipids (red). Magnification: 100×.
Figure 2:
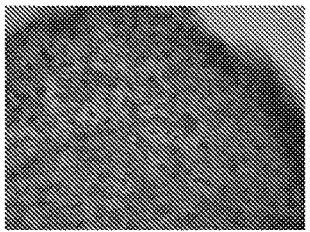
Figure 2:
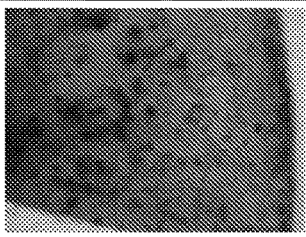
Figure 2:
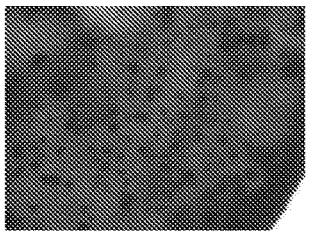
Figure 2:
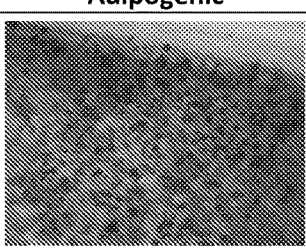
Figure 2:
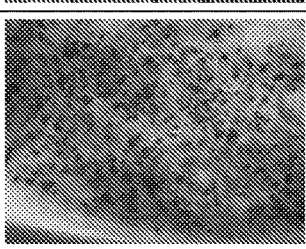

FIG. 2 demonstrates lineage-specific staining of hydrogel cross-sections after tri-lineage induction for 21 days in vitro. Safranin O detects deposition of cartilage extracellular matrix glycosaminoglycans (stained red), Alizarin red highlights calcium deposition, while Oil Red O was used to evidence lipids within differentiated cells. Intense staining was obtained for the three lineages within the gellan gum based hydrogels.

These results clearly indicate that the disclosed gellan gum-based hydrogels are able to maintain high cell viability up to at least three weeks after encapsulation. Furthermore, the gellan gum-based hydrogels are able to promote differentiation into each of the three possible lineages.

The following examples are merely illustrative and should not be construed to limit the scope of the disclosure. Alternative approaches will be obvious to those skilled in the art.

Example 1. Purification of Commercial Gellan Gum

In an embodiment, commercial gellan gum was purified with slight modifications of a reported procedure (Doner, 1997). Commercial gellan gum (Sigma, 5 g) was dissolved in distilled water with heating. Amberlyst IR-120 ($H^+$ form) ion exchange resin was added during 30 minutes until the solution pH stabilized at approximately 2.4. The solution was allowed to stir at 60° C. for ten minutes then filtered to remove the resin. To the filtrate was added aqueous sodium hydroxide solution until pH reached 8.5. The solution was poured onto ethanol, forming a precipitate. After stirring at room temperature for 1 hour, the liquid phase was decanted off and the remaining precipitate was filtered, dissolved in distilled water and dialysed against distilled water. After freezing and freeze-drying, the purified gellan gum was obtained as a white solid, 3.2 g.

Example 2. Sulphation of Purified Gellan Gum

In an embodiment, 500 mg of purified gellan gum were added to 50 mL of N,N-dimethylacetamide at 60° C. with stirring. Then, 10 molar equivalents of pyridine-sulphur trioxide complex (1.205 g) were added to the solution which was left to stir for two days at 50° C. When the solution was completely dissolved, it was left to cool down while stirring.

Using an ice bath, the temperature of the solution was maintained below 30° C. and 20 mL of $H_2O$ were added. Then NaOH (1 M) was added to ensure the pH increased to around 10. Afterwards, the solution was left to stir for 1 hour at RT and then dialysed against distilled water for 5 days. After freezing and freeze-drying, the product was obtained as a white solid, 573 mg.

Example 3. Methacrylation of Purified Gellan Gum

In an embodiment, 500 mg of purified gellan gum were dissolved in 50 mL of $H_2O$ and aqueous NaOH (1 M) was added to ensure the pH was around 9. Then, 1850 µL of glycidyl methacrylate were added to the solution and the pH was maintained between 8.5 and 10 with aqueous NaOH (1 M). When the pH was stable, precipitation was carried out by adding 20 mL of cold acetone (4° C.) to the solution. The acetone was decanted and the precipitate was dissolved in 20 mL of $H_2O$ and dialysed. After dialysis against distilled water, the solution was frozen and then freeze-dried give the product as a white solid 513 mg.

Example 4. Modification of Purified Gellan Gum with Azelaic Dihydrazide

In an embodiment, 500 mg of purified gellan gum were weighed and suspended in 50 mL of MES (0.1 M) at RT and 5 molar equivalents of DTMMCl (1.03 g) dissolved in 4 mL of MES (0.1 M) was added to the solution which was then left to stir for 30 minutes. Meanwhile, 5 molar equivalents of azelaic dihydrazide (0.81 g) dissolved in 4 mL of MES (0.1 M) and then added dropwise to the solution which was left to stir for 24 hours at RT. Then, aqueous NaOH solution (1 M) was added until the pH reached around 10. Finally, the solution was dialysed against distilled water then frozen and freeze-dried to give the product as a white solid, 766.4 mg.

Example 5. Alternative Methacrylation of Gellan Gum

In an embodiment, purified gellan gum (153 mg) was dissolved in DMSO (10 mL) at 60° C. and triethylamine (78 µL) was added followed by a spatula tip of DMAP. Methacrylic anhydride (0.078 mL) was added and the mixture was stirred at RT overnight, then poured onto ethanol. After standing for 30 minutes, the solvent was decanted and the precipitate was dissolved in distilled water and dialysed. After dialysis, the solution was frozen and freeze-dried to give the product as a white solid, 146 mg.

Example 6. In Vitro Tri-Lineage Differentiation of Human Adipose Mesenchymal Stromal/Stem Cells (hASC) within Gellan Gum (GG)-Based Hydrogels In an embodiment, differentiation of mesenchymal stem cells within tissue-specific lineages is commonly evaluated by the deposition of tissue-specific extracellular matrix (ECM) components. Herein, expression of these ECM markers was evaluated upon in vitro tri-lineage induction of hASC when encapsulated in GG-based hydrogels.

In an embodiment, human adipose mesenchymal stromal/stem cells (hASC), produced in xeno-free conditions, were expanded and isolated as single cells for mixture with gellan-gum based aqueous solution. Gellan gum-based polysaccharides, in powder form, were solubilized with distilled water in order to obtain 1.25% w/V-2.5% w/V solutions. Cells were added to this solution at a 2:8 ratio (cells:polymer) at physiological temperature (37° C.). A final cell density of 5 million cells/mL hydrogel was obtained. The cellular polymer suspension was dispensed as individual 20 µL disks, and further reticulated with cell culture media. Such hydrogel disks were in vitro cultured for 21 days with chondrogenic, osteogenic or adipogenic growth factors. Cell viability was assessed by live/dead staining (FIG. 1) while ECM deposition was determined by lineage specific stainings (FIG. 2).

The gellan gum disclose in the present subject-matter is an autonomous biomaterial for human adipose stem cells (hASCs) differentiation in the osteogenic lineage, acting by a mechanism dependent on a mechanotransduction pathway in the absence of any further biological or biochemical cue. It was surprisingly show an autonomous osteogenic activity of a hydrogel based on a gellan gum of the present subject matter, preferably a methacrylated gellan, without the modification of the material with cell-adhesive peptides, other cell-adhesion motifs or mineralization cues.

The term "comprising" whenever used in this document is intended to indicate the presence of stated features, integers, steps, components, but not to preclude the presence or addition of one or more other features, integers, steps, components or groups thereof.

All references recited in this document are incorporated herein in their entirety by reference, as if each and every reference had been incorporated by reference individually.

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The above described embodiments are combinable.

The following claims further set out particular embodiments of the disclosure.

REFERENCES

Coutinho, D. F., Sant, S., Shin, H., Oliveira, J. T., Gomes, M. E., Neves, N. N., Khademhosseini, A. & Reis, R. L. (2010) Modified gellan gum hydrogels with tunable physical and mechanical properties. Biomaterials, 31(29), 7494-7502.

D'Este, M., Eglin, D. & Alini, M. (2014) Carbohydrate Polymers, 108, 239-246.

Doner, W. (1997) Rapid purification of commercial gellan gum to highly soluble and gellable monovalent cation salts. Carbohydrate Polymers, 32, 245-247.

Hamcerencu, M., Desbrieres, J., Khoukh, A., Popa, M & Riess, G. (2008) Synthesis and characterization of new unsaturated esters of gellan gum. Carbohydrate Polymers, 71, 92-100.

Oliveira, J. T., Santos, T. C., Martins, I., Picciochi, R., Marques, A. P., Castro A. G., Neves, N. N., Mano, J. F. & Reis, R. L. (2009) Gellan gum injectable hydrogels for cartilage tissue engineering applications: In vitro studies and preliminary in vivo evaluation. Tissue Engineering Part A. 16(1): 343-353.

Rada, T., Carvalho, P. P., santos, T. C., Castro, A. G., Reis, R. L. & Gomes, M. E. (2013) Chondrogenic potential of two hASCs subpopulations loaded onto gellan gum hydrogel evaluated in a nude mice model. Curr. Stem Cell Res. Ther., 8(5): 357-364.

Recuenco, F. C., Kobayashi, K., Ishiwa, A., Enomoto-Rogers, Y., Fundador, N. G., Sugi, T., Takemae, H., Iwanaga, T., Murakoshi, F., Gong, H., Inomata, A., Horimoto, T., Iwata, T. & Kato, K. (2014) Gellan sulphate inhibits *Plasmodium falciparum* growth and invasion of red blood cells in vitro. Sci. Rep., 4, 4723.

Silva-Correia, J., Oliveira, J. M., Caridade, S. G., Oliveira, J. T., Sousa, R. A., Mano, J. F. and Reis, R. L. (2011) Gellan gum hydrogels for intervertebral disc tissue-engineering applications. J. Tissue Engineering and Regenerative Medicine, 5, 97-107.

The invention claimed is:

1. A gellan gum for promoting chondrogenic and/or osteogenic and/or adipogenic differentiation of human mesenchymal stem cells, the gellan gum represented by the structure according to Formula I

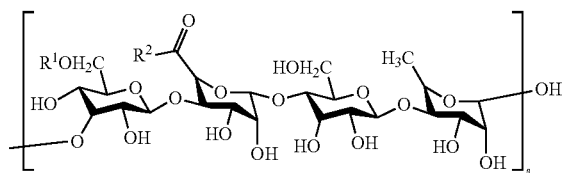

Formula I wherein $R^1$ is hydrogen and $R^2$ is NHNHCO(CH$_2$)n'CONHNH$_2$, wherein n' is an integer chosen from 1 to 10.

2. The gellan gum of claim 1, wherein the gellan gum is suitable for treating diseases that are positively influenced by the chondrogenic and/or osteogenic and/or adipogenic differentiation of human mesenchymal stem cells.

3. The gellan gum of claim 1, wherein the gellan gum promotes bone repair.

4. The gellan gum of claim 1, wherein the gellan gum is suitable for treating bone fractures, promoting bone repair or treating osteopathies or osteochondritis.

5. The gellan gum of claim 1, wherein n is an integer from 700 to 4000.

6. The gellan gum of claim 1, wherein the degree of substitution by $R^2$ is between 0.5-20%.

7. A hydrogel comprising the gellan gum of claim 6, and a suitable solvent.

8. The hydrogel of claim 7, further comprising photo crosslinking, ionic crosslinking, or mixtures thereof.

9. The hydrogel of claim 7, wherein the concentration of the gellan gum is between 0.5%-5% w/V.

10. The hydrogel of claim 9, wherein the concentration of the gellan gum is between 0.5%-2% w/V.

11. A composition for the treatment of diseases that are positively influenced by chondrogenic and/or osteogenic and/or adipogenic differentiation of human mesenchymal stem cells, comprising a matrix comprising the gellan gum of claim 6 or the hydrogel of claim 7, and human adipose mesenchymal stromal/stem cells.

12. The composition of claim 11, wherein the human adipose mesenchymal stromal/stem cells are encapsulated within the gellan gum.

13. The composition of claim 11, wherein the composition is in an injectable form.

14. The composition of claim 11, wherein the composition is suitable for inclusion in a mesh, disc, scaffold or membrane.

15. The hydrogel of claim 7, wherein the solvent is an aqueous solvent.

* * * * *